United States Patent
Lele et al.

(10) Patent No.: US 6,369,249 B1
(45) Date of Patent: *Apr. 9, 2002

(54) PROCESS FOR THE PREPARATION OF N-SUBSTITUTED ACRYLAMIDES

(75) Inventors: Bhalchandra Shripad Lele; Mohan Gopalkrishna Kulkarni, both of Maharashtra (IN)

(73) Assignee: Council of Scientific & Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/495,909

(22) Filed: Feb. 2, 2000

(51) Int. Cl.$^7$ ............................................. C07C 231/02
(52) U.S. Cl. .......................... 554/69; 554/35; 564/143; 564/204
(58) Field of Search ................................. 564/143, 204; 554/35, 69

(56) References Cited

FOREIGN PATENT DOCUMENTS

GB          2092136      *  9/1982

OTHER PUBLICATIONS

Finar, I. L., Organic Chemistry, vol. one, p. 529, 1964.*

* cited by examiner

Primary Examiner—Shailendra Kumar
(74) Attorney, Agent, or Firm—Dickinson Wright PLLC

(57) ABSTRACT

The present invention relates to a process for the preparation of N-substituted acrylamides of the general formula $CH_2=CH-CONHR$, wherein, R is alkyl group having carbon 1 to 22 or acyl group having carbon 1 to 18. The process for the preparation of the N-substituted acrylamides comprises reacting acrylamide with alkyl acyl chloride in the presence of Lewis acid catalyst in an organic solvent at a temperature ranging between room temperature to 50° C. for a period ranging between 1 hour to 24 hours.

7 Claims, No Drawings

PROCESS FOR THE PREPARATION OF N-SUBSTITUTED ACRYLAMIDES

FIELD OF INVENTION

This invention relates to a process for the preparation of N-substituted acrylamides. More particularly it relates to an improved process for the preparation of N-substituted acrylamides of the general formula $CH_2=CH-CONHR$, wherein, R is alkyl group having carbon 1 to 22 or acyl group having carbon 1 to 18 by Friedel-Craft's alkylation and acylation of acrylamide respectively, in the presence of a Lewis acid catalyst.

BACKGROUND OF THE INVENTION

Copolymers of N-alkylacrylamides with various other monomers are finding diverse applications as follows:
1) Poly (β napthyl 6 acrylamidocaproate-co-acrylic acid) as plant growth regulator (C.J. Boundreaux, W. C. Bunyard and C. L. Mccormick, J. Controlled Rel. 40,223 (1996).
2) Poly (N-dodecylacrylamide-co-N-methyl 4vinyl pyridinium Na) as salt resistant viscosity builder (D. Christine, B. Alain and L. Pierre, Macromol. Symp. 102,233 (1995), D. Christine, B. Alain, B. Fransis and V. M. Laure, Polymer 36,2095 (1995).
3) Poly (N-stearoyl acrylamide-co-2(3-acrylamidopropyl) dimethyl aminoethyl isoproply phosphate) as phosphatidylcholine analogous material (W. Yenfeng, C. Tianming, K. Masaya and N. Taiao, J. Polym. Sci. Chem. Edn. 34,449 (1996).
4) Poly (N-tert-octylacrylamide-co-N-alkylacrylamide) as thickner in cosmetics (J. Mondet and B. Lion Eur. Pat. Appl. EP 494,022.
5) Poly (N-octylacrylamide-co-3 acrylamido-3 methyl butanoate Na) for oil recovery (A. Kitagawa and T. Koichi, Jpn. Kokai Tokkyo Koho JP 07,188,347) and so on.

Crosslinked hydrogels based on N-alkylacrylamides also find various applications such as thermosensetive polymeric drug carriers (C. L. Mecormick and J. C. Brent, Polym. Mater. Sci. Eng. 55,366 (1986), M. Akashi, A. Kishida, S. Sakuma and H. Kikuchi, PCT Int. Appln. WO 9730730. H. Yu and D. W. Grainger, Polym. Prepr. 34,820 (1993), materials for hard contact lenses (S. Q. Zhou, L. Xiugao and Y. Wang PCT Intl. Appln. WO 9735,896), concentration of aqueous protein solutions (J. Manrong. Z. Guiying, W. Changfa, L. Peiyi and H. Wei, Gaofenzi Xubao 3, 321 (1995), Stationary phases for HPLC ((N. Shoji, I. Hirotaka and H. Chuichi, Polymer J. (Tokkyo 25, 609 (1993)) etc.

In order to meet these growing demands of N-alkylacrylamides. various methods for their synthesis have been developed. These methods can broadly be classified into three types viz.
1) Reaction of acryloyl chloride with alkyl amine,
2) Pyrolysis or thermal decomposition of carboxylic acid amides, and
3) Reaction of olefins with nitriles.

The above mentioned processes are described in brief hereinbelow:
Methods of Type 1
Reaction of Acryloyl Chloride with Alkylamine In this method N-alkylacrylamides are synthesized by reacting acryloyl chloride with alkyl amines in the presence of acid quencher i.e. triethyl amine at 0° C. (C. G. Overberger, C. Frazier and J. Mandehman, J. Am. Chem. Soc. 75,3326 (1953), J. Lal and G. S. Trick, J. Polym. Sci. A2, 4559 (1964), E. F. Jr. Jordan, G. R. Riser and B. Artymyshyn, J. Appl. Polym. Sci. 13,1777 (1969), K. J. Shea, G. J. Stoddard, D. M. Shavelle, F. Wakui and R. M. Chaote, Macromolecules 23,4497 (1990).
Methods of Type 2
Thermal Decomposition of Carboxylic Acid Amides.

A number of patents which are based on this technique have been filed. A Japanese patent No. Jpn. Kokai Tokkyo JP 07,145122, discloses the synthesis of N,N diethylacrylamide as follows. Methyl acrylate was reacted with diethylamine to give Michael addition product methyl β N,N diethylaminopropionate. This was treated with sodium methoxide for 46 hrs and then with phosphoric acid for 1 hr. at 50° C. to give N,N diethyl β diethylaminopropionic acid amide which was then thermally decomposed at 180° C. and 100 torr pressure for 4 hrs. to give N,N diethylacrylamide (K. Motomasu, I. Seiichi and I. Massasane, Jpn. Kokai Tokkyo Koho JP 07,145 122). Similar process for the synthesis of N,N dialkyl acryl and methacrylamides has been reported wherein, thermal decomposition of carboxylic acid amide was carried out in the presence of $H_2SO_4$ at 195° C. (T. Maruyama, 0. Kido, I. Okidaka and R. Hiraoka, Jpn. Kokai Tokkyo Koho JP 04,208 258).

N-alkylacrylamides have also been synthesized by amidation of bicyclic carboxylic acids followed by the thermal decomposition of the carboxamide. Thus N,N dimethylacrylamide was synthesized by reacting dimethylamine with bicyclo [2.2.1]hept-2-ene-2-carboxylic acid in autoclave to give N,N dimethyl bicyclo [2.2.1]hept-2ene-2-carboxylic acid in autoclave to give N,N dimethyl bicyclo [2.2.1]hept-2-ene-2-carboxamide, followed by its thermal decomposition at 200° C. in vacuo (A. Ohshima and K. Tsubashima Jpn. Tokkyo Koho 7909 170, A. Oshima, K. Tsubashima and N. Takahashi Ger. Offen. 2,217,623). The use of pyrolysis for preparation of N-alkylacrylamides has also been reported. In this, N(1,1 dimethyl 1-3 oxybutyl)-3 methoxy propionamide was hydrogenated in the presence of dimethylamine p-toluenesulfonic acid and Pt. catalyst to give N(1,1 dimethyl -3 dimethyl aminobutyl) 3 methoxy propionamide. This was heated with NaOH at 80 to 90° C. for 3 hrs to give N(1,1dimethyl-3 dimethylaminobutyl) acrylamide (D. I. Hoke, U.S. Pat. No. 3,943,114).
Methods of Type 3
Reaction of Olefins with Nitriles N-alkylacrylamides have also been synthesized by reacting acrylonitrile with various olefins. A Japanese patent No. Japan Kokai 7391011 discloses the synthesis of N-tertoctylacrylamide by reacting acrylonitrile with 2,4,4 trimethyl 1-pentene at 40° C. for 3 hrs using 65% $H_2SO_4$ as solvent (T. Takada, Y. Kawakatsu, T. Mihamisawa and K. Hara, Japan Kokai-7391011). Similarly, acrylonitrile has been reacted with dimethylamine at 200° C. in the presence of Lewis acid $ZnCl_2$ to give N,N dimethylacrylamide (Asahi Chemical Ind. Co. Ltd. Fr. 2,046 122). N-alkylacrylamide has also been synthesized by oxidative carbonylation. In this, $PdCl_2$, $CuCl_2$, CuCl and propylamine in 1:10:10:120 ratio were treated with methane, carbon monoxide and oxygen to give N-propylacrylamide (G. Biale U.S. Pat. No. 3,523,971).

Amongst the above sighted processes for preparation of alkylacrylamides, methods of the type 1) cannot be used to synthesize N-acylacrylamides, monomers, that are gaining increasing importance. Besides, it is also not attractive for large scale productions since it uses acryloyl chloride which is an expensive and hazardous reagent.

Other processes sighted for the preparation of alkylacrylamides i.e. methods of type 2) and 3) suffer from the drawbacks of harsh reaction condition such as high temperatures, high vacuum and tedious work up procedures. Also in most of the cases N-alkylacrylamide with small alkyl chain length were synthesized.

OBJECTS OF THE INVENTION

It is therefore an object of the present invention to provide process for the preparation of N-substituted acrylamides.

Another object of the present invention is to provide a process with mild reaction conditions such as reaction at room temperature and atmospheric (normal) pressure which will obviate tedious work up procedures used in the conventional processes.

It is also an object of the present invention that such a process be applicable for the preparation of N-substituted acrylamides with long alkyl chain length.

SUMMARY OF THE INVENTION

Friedel-Craft's alkylation is an effective and convenient method which is widely used to synthesize linear alkyl benzenes (LABs). Despite this, its use in the synthesis of N-alkylacrylamides has not been reported yet. It has now been found that N-alkylacrylamides and N-acylacrylamides can be produced in high yields by alkylation and acylation of acrylamide respectively, in the presence of a Lewis acid catalyst in suitable solvent at room temperature and atmospheric pressure.

DETAILED DESCRIPTION OF THE INVENTION

Accordingly the present invention provides an improved process for the preparation of N-substituted acrylamides of the general formula $CH_2=CH-CONHR$ wherein, R is alkyl group having carbon 1 to 22 or R is acyl group having carbon 1 to 18 which comprises reacting acrylamide with alkyl/acyl chloride in the presence of a Lewis acid catalyst in an organic solvent at a temperature ranging between room temperature to 50° C. for a period ranging between 1 hour to 24 hours, terminating the reaction if necessary and cooling to ambient temperature, pouring the mixture in a non-solvent to obtain the precipitated product-N-substituted acrylamide.

In one of the embodiment of the present invention acrylamide used may be such as compounds of the formula $CH_2=CR-CONH_2$, wherein, R is hydrogen or methyl.

In another embodiment alkyl chloride used may be such as compounds of the formula $CH_3-(CH_2)n-Cl$, wherein, n is an integer from 0 to 21 and the alkyl chloride may be prepared by treating corresponding alcohol with thionyl chloride.

In yet another embodiment acyl chloride used may be such as compounds of the formula $CH_3-(CH_2)n-COCl$, wherein, n is an integer from 0 to 16 and the acyl chloride may be prepared by treating corresponding acid with thionyl chloride.

In still another embodiment Lewis acid catalyst used may be metal chlorides such as aluminium chloride, zinc chloride, nickel chloride.

In an another embodiment the solvent used may be such as acetonitrile, tetrahydrofuran, acetone, nitrobenzene, dioxane.

In an another embodiment the non-solvent used may be such as water, hexane, diethyl ether.

In a feature of the present invention, the process is typically carried out under mild conditions. Stoichiometric amounts of acrylamide and alkyl chloride or acyl chloride are dissolved in a suitable solvent and the stoichiometric amount of a Lewis acid catalyst is added and the reaction mixture is stirred at room temperature for 5 to 10 minutes. This is followed by vigorous evolution of hydrogen chloride gas formed due to N-alkylation or N-acylation of acrylamide. Reaction is exothermic which increases the temperature of reaction mixture from room temperature to 40 to 50° C. After the evolution of hydrogen chloride ceases, the reaction mixture is cooled down to room temperature and poured into another solvent which is a nonsolvent for the product i.e. N-substituted acrylamide Precipitated N-substituted acrylamide is then isolated.

The ranges and limitations provided in the instant specification and claims are those which are believed to particularly point out and distinctly claim the present invention. It is however understood that other ranges and limitations which perform substantially the same function in the same or substantially the same manner to obtain the same or substantially the same results are intended to be within the scope of the instant invention as defined by the instant specification and claims.

The process of the instant invention will be further described by the following embodiments which are provided for illustration and are not to be construed as limiting the invention.

EXAMPLE 1

Preparation of N-cetylacrylamide

In a 250 ml capacity conical flask 13 g cetyl chloride (0.05 M), 3.5 g acrylamide (0.05 M) and 50 ml acetone were placed to obtain a clear solution. The solution was stirred with a magnetic needle at room temperature. 6.5 g anhydrous aluminium chloride (0.05 M) was added and the reaction mixture was stirred at room temperature. After 5 to 10 minutes of stirring, vigorous evolution of hydrogen chloride took place which ceased after about 5 minutes. Temperature of the reaction mixture was raised to 40 to 50° C. It was then cooled to room temperature and poured into 500 ml cold water. White product was precipitated. The product was isolated and purified by reprecipitation from acetone into cold water.

Yield 65%.

EXAMPLE 2

Synthesis of N-Behenylacrylamide

In a 250 ml capacity conical flask 8.63 g behenyl chloride (0.025 M), 1.75 g acrylamide (0.025 M) and 50 ml acetone were placed to obtain a clear solution. The solution was stirred with a magnetic needle at room temperature. 3.25 g anhydrous aluminium chloride (0.025 M) was added and the reaction mixture was stirred at room temperature. After 5 to 10 minutes of stirring vigorous evolution of hydrogen chloride took place which ceased after about 5 minutes. The product was isolated following the procedure described for synthesis of N-cetylacrylamide.

Yield 83%.

EXAMPLE 3

Synthesis of N-Dodecanoylacrylamide

In a 250 ml capacity conical flask 10.9 g dodecanoyl chloride (0.05 M), 3.5 g acrylamide (0.05 M) and 50 ml acetone were placed to obtain a clear solution. The solution was stirred with a magnetic needle at room temperature. 6.5 g anhydrous aluminium chloride (0.05 M) was added and the reaction mixture was stirred at room temperature. After 5 to 10 minutes of stirring, vigorous evolution of hydrogen chloride took place which ceased after about 5 minutes. The product was isolated following the procedure described for synthesis of N-cetylacrylamide.

Yield 50%.

EXAMPLE 4
Synthesis of N-Stearoylacrylamide

In a 250 ml capacity conical flask 15.1 g stearoyl chloride (0.05 M), 3.5 g acrylamide (0.05 M) and 50 ml acetone were placed to obtain a clear solution. The solution was stirred with a magnetic needle at room temperature. 6.5. g anhydrous aluminium chloride (0.05 M) was added and the reaction mixture was stirred at room temperature. After 5 to 10 minutes of stirring vigorous evolution of hydrogen chloride took place which ceased after about 5 minutes. The product was isolated following the procedure described for synthesis of N-cetylacrylamide.

Yield 80%.

EXAMPLE 5
Synthesis of N-Octadecanoylacrylamide

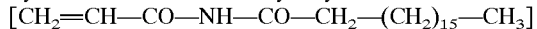

Into a 250 -mL-capacity conical flask equipped with an anhydrous calcium chloride ($CaCl_2$) guard tube, 15.1 g 1-octadecanoyl chloride [$CH_3$—$(CH_2)_{16}$—COCl] (0.005 M). 3.5 g acrylamide ($CH_2$=CH—CO—$NH_2$) (0.05 M), and 50 ml acetone were placed to obtained a clear solution. The solution was stirred with a magnetic needle at room temperature. Anhydrous zinc chloride ($ZnCl_2$), 6.5 g (0.05 M), was added and the reaction mixture was stirred at room temperature. After 5–10 min of stirring, vigorous evolution of hydrogen chloride took place which ceased after about 5 min. The temperature of reaction mixture was increased to 40–50° C. It was then cooled to room temperature and poured into 500 ml cold distilled water. A white product precipitated. The product was isolated and purified by reprecipitation from acetone into cold water. The purified product was dried in a vacuum desiccator.

Yield: 75%.
Melting point: 56° C.
IR (nujol): 1622 $cm^{-1}$ (-c=c-), 1652 $cm^{-1}$ (amide carbonyl)

The main advantages of the present invention are:
1. The process of the present invention is applicable for the synthesis of N-acylacrylamides as well as N-alkylacrylamides unlike other processes reported in the literature.
2. The reaction conditions are very mild and the time required for reactions to complete is very short in comparison to other processes reported in the literature.
3. The process of the present invention is applicable for the synthesis of N-alkyl/N-acyl acrylamides of small as well as long alkyl/acyl chain unlike the other processes reported in the literature for synthesis of N-alkyl/N-acyl acrylamides with small alkyl chain lengths.

We claim:

1. An improved process the preparation of N-substituted acrylamides of the general formula $CH_2$=CH—CONHR wherein, R is alkyl group having carbon 1 to 22 or R is acyl group having carbon 1 to 18 which comprises reacting acrylamide with an alkyl or/acyl chloride in the presence of a Lewis acid catalyst in an organic solvent at a temperature ranging between room temperature to 50° C. for a period ranging between 1 hour to 24 hours, terminating the reaction if necessary and cooling to ambient temperature, pouring the mixture in a non-solvent to obtain the precipitated product- N-substituted acrylamide.

2. An improved process as claimed in claim 1 wherein, acrylamide used is selected from compounds of the formula $CH_2$=CR—$CONH_2$, wherein, R is hydrogen or methyl.

3. An improved process as claimed in claim 1 wherein, alkyl chloride used is selected from compounds of the formula $CH_3$—$(CH_2)$n-Cl, wherein, n is an integer from 0 to 21 and the alkyl chloride may be prepared by treating corresponding alcohol with thionyl chloride.

4. An improved process as claimed in claim 1 wherein, acyl chloride used is selected from compounds of the formula $CH_3$—$(CH_2)$n-COCl, wherein, n is an integer from 0 to 16 and the acyl chloride may be prepared by treating corresponding acid with thionyl chloride.

5. An improved process as claimed in claim 1 wherein, Lewis acid catalyst used is selected from metal chlorides from the group consisting of aluminium chloride, zinc chloride, nickel chloride.

6. An improved process as claimed in claim 1 wherein, the solvent used is selected from the group consisting of acetonitrile, tetrahydrofuran, acetone, nitrobenzene, dioxane.

7. An improved process as claimed in claim 1 wherein, the non-solvent used is such as water, hexane, diethyl ether.

* * * * *